(12) United States Patent
Abdelmalek (10) Patent No.: US 8,376,930 B2
(45) Date of Patent: Feb. 19, 2013

(54) IMPLANTABLE PUMP FOR ERECTILE DYSFUNCTION TREATMENT

(76) Inventor: Fawzy T. Abdelmalek, St. Louis, MO (US)

( * ) Notice: Subject to any disclaimer, the term of this patent is extended or adjusted under 35 U.S.C. 154(b) by 1099 days.

(21) Appl. No.: 12/240,388

(22) Filed: Sep. 29, 2008

(65) Prior Publication Data

US 2009/0209808 A1    Aug. 20, 2009

Related U.S. Application Data

(60) Provisional application No. 60/976,061, filed on Sep. 28, 2007.

(51) Int. Cl.
*A61F 5/00*    (2006.01)
(52) U.S. Cl. ........................................... 600/40
(58) Field of Classification Search ............... 600/38–41; 128/897, 898
See application file for complete search history.

(56) References Cited

U.S. PATENT DOCUMENTS

| | | | | |
|---|---|---|---|---|
| 2,357,238 A * | 8/1944 | Trimble | ..................... | 607/92 |
| 5,048,511 A * | 9/1991 | Rosenbluth et al. | ............ | 600/40 |
| 5,267,940 A * | 12/1993 | Moulder | ..................... | 600/16 |
| 6,200,260 B1 * | 3/2001 | Bolling | ..................... | 600/16 |

* cited by examiner

*Primary Examiner* — Samuel Gilbert
(74) *Attorney, Agent, or Firm* — Grace J. Fishel (57) ABSTRACT

An implantable system for erectile dysfunction treatment includes an implantable pump having an inlet and an outlet port. The inlet port is configured to receive blood from an artery within the body. The outlet port is configured to receive the blood from the inlet port and deliver that blood to an artery having a direct or indirect path to the corpora cavernosa of the penis. Activation of the pump, preferably via manual compression or electrical activation, causes the transfer of blood and ultimately an erection. Upon conclusion of sexual activity, blood drains from the penis in a normal manner and returns the penis to a flaccid state. The pump preferably incorporates a non-return valve to prevent backflow of blood from outlet port to inlet port.

12 Claims, 5 Drawing Sheets

IMPLANTABLE PUMP FOR ERECTILE DYSFUNCTION TREATMENT

CLAIM TO PRIORITY

The present application claims priority to U.S. Provisional Patent Application No. 60/976,061, filed Sep. 28, 2007 and entitled "Implantable Pump for Erectile Dysfunction Treatment." The identified provisional patent application is hereby incorporated by reference in its entirety.

BACKGROUND OF THE INVENTION

1. Field of the Invention

This invention relates generally to a method and device for alleviating erectile impotency, and especially to a surgically implantable pump device that may be implanted to facilitate injecting blood to inflate the corpus cavernosum of the penis. An implantable pump assembly includes a blood inlet artery connection, a blood receiving chamber, a non-return valve, a blood ejection elastic compression chamber and an outlet artery connection.

Briefly the invention discloses a pump assembly designed to be surgically connected to an internal artery to increase the influx of blood flow to the dorsal and deep arteries that feeds the penis. The pump assembly is to be implanted in the lower part of the abdomen in a way that will not prevent normal flow of the blood. Upon pressing the elastic enclosure of a compression chamber, a non-return valve closes and an influx of blood is injected to flow into the dorsal and deep arteries of the penis. Upon releasing of the compression chamber, the compression chamber springs back to its original shape, the non-return valve opens and the blood is drawn into the compression chamber. Repeated act of pressing and releasing the compression chamber result in forced injections of the blood influx into the penis organ that quickly cause erection. In addition to the normal blood flow to the penis, the pump draws blood from an internal pudendal artery and inject it into the than the dorsal and deep arteries of the penis. An increased flow of blood delivered to the penis will not restrict the normal flow at any time but provide an adequate influx of blood when needed. Upon conclusion of the sexual activity and withdrawal, the blood drains naturally through the dorsal vein and the penis returns to its normal flaccid condition.

2. Brief Description of the Background of the Art

Erectile Dysfunction (ED) is defined as the inability of a man to attain or sustain an erection sufficient for sexual intercourse or when a man has problems getting or maintaining an erection long enough for sex. It happens when not enough blood flows to the penis that can be persistent condition. ED isn't the same for all men; some men aren't able to get an erection at all, others can get one, but it's not hard enough for sex. Others get a hard erection but lose it before or during sex. ED is a medical condition due to several causes impairing blood flow to the penis, so in many cases erections will not improve without treatment.

Common treatments aim to increase blood flow into the penis to cause erection, these treatments include: Drugs, Needle injection therapy, self administered intrauethral therapy, use of vacuum devices and vascular surgery.

Drug treatments similar to Sildenafil (Viagra), Tadalafil (Cialis), and Vardenafil (Levitra) are prescribed by physicians to ED patients. These drugs enhance the effects of nitric oxide, a chemical messenger that relaxes smooth muscles in the penis. This increases the amount of blood and allows a natural sequence to occur for an erection in response to sexual simulation. It is known that these drugs can cause common side effects similar to headache, facial flushing, and upset stomach and less commonly, bulrush vision, blurred vision or sensitivity to light may occur. Physicians must administer and determine the dose for patients that have liver or kidney problems, taking prostate inhibitor, have high blood pressure or have previous history of heart attack, stroke or life-threatening heart rhythm.

In needle-injection therapy method, the patient uses a fine needle to inject a drug called Alprostadil (al-pros-tuh-dil) into the base or side of his penis. This generally produces an erection in five to 20 minutes that lasts about an hour. Because the injection goes directly into the spongy cylinders that fill with blood, alporstadil is an effective treatment for many men. Side effects may include bleeding from injection, prolonged erection and formation of fibrous tissue at the injection site. The cost per injection can be expensive. Other lesser expensive injection drugs include Papaverine and Phentlamine (Regitne).

The self-administered intraurethral therapy is known as Medicated Urethral System for Erection (MUSE). The patient uses a disposable applicator to insert a tiny suppository about half the size of a grain of rice into the tip of his penis. The suppository is placed about two inches in the penis is absorbed by erectile tissue increasing the blood flow that causes an erection. Although needles are not used, this method can be painful or uncomfortable, side effects may include pain, minor bleeding in the urethral, dizziness and formation of fibrous tissue.

The treatment of Vacuum devices involves the use of an external vacuum and one or more rubber bands (tension rings). The patient places a hollow plastic tube and pulls blood into the penis. Once he achieves an adequate erection, he slips a tension ring around the base of his penis to maintain the erection. He then removes the vacuum device. The erection typically lasts long enough to have adequate sexual intercourse; he then removes the tension ring after conclusion of the sexual relation.

The vascular surgery treatment method involves surgically placing a device into the two sides of the penis, allowing erection to occur as often and as long as desired. These implants consist of either an inflatable device or semi-rigid rods made from silicon or polyurethane and the use of an inflatable pump, a working fluid, a reservoir capable of holding the fluid and communicating tubes and isolation valves. This treatment is often complicated, expensive and is usually not recommended until other methods have been considered or tried first. As with any surgery, there is a small risk of complications such as infection.

Buuck, in U.S. Pat. No. 3,954,102 describes two expandable cylinders implanted in the penis; replacing the function of the two corpora cavernosa and using working fluid, a reservoir and a transfer pump located in the scrotum to pressurize and transfer the fluid to the expandable cylinders to achieve erection.

Fischell, in U.S. Pat. No. 4,559,931, describes another manually actuated, fluid driven, inflatable penile prosthesis with two cylinders in the coropa caverosa. A diaphragm pump actuator and pressure release chamber are adapted and implanted in the abdomen cavity to be manipulated through the skin of the patient to control the fluid pressure in the system.

Other U.S. patents similar to U.S. Pat. Nos. 4,590,927, 6,723,042, 6,730,017, 6,808,490, they document several implantable penile prosthesis systems, pump devices, valves, connectors and improvements, however they offer mechanical hydraulic driven systems that require to effectively replace the biological function of the corpora cavernosa of the penis.

It is known that penile implants eliminates the possibility of return of natural erections and may require repeated surgery due to infections, erosions, or mechanical problems with the implanted penile device.

The present invention maintains the biological function of the corpa cavernosa for achieving penile erection and keeps the blood flow to and from the penis. The invented penile erectile implant system effectively treats erectile dysfunction due to lack of adequate flow of blood needed for the penis erection. The implant provides means to increase the blood pressure and increase its flow to effect inflation of the corpora cavernosa of the penis. Like that of the normal physiological process, upon achieving orgasm, the blood drains from the penis tissue.

In the present invention as in any human device implant surgeries, risk of blood coagulation is a concern, medical attention and treatment using anti-coagulant drugs may be required to prevent possible blood coagulation problems.

SUMMARY OF THE INVENTION

The present invention provides a dependable pump system to be surgically implanted inside the body and connected to an artery that supplies blood to the corpora cavernosa of the penis. The pump is relatively small and can be implanted in the body on the right side or the left side of the penis at the lower part of the abdomen. Tissues in the shaft of the penis normally trap blood increasing the pressure within the penis and causing it to erect and become firm. Following orgasm or the withdrawal, the process is reversed and the blood flows out of the penis back into circulation, so the penis deflates to a flaccid condition.

In the present invention an erection occurs when the blood is pumped to increase the flow of the blood into the penis to cause and maintain an erection. It generally happens when the patient repeatedly presses and releases the elastic compression chamber of the pump enclosure to cause an influx of blood to flow into the blood vessels which surround the penis organ and cause it to inflate to a hard rigid condition.

The relatively small implant and the simple use of the device just by applying repeated pressing and releasing the compressible chamber of the pump will enable the user to maintain erection as long as he desires. Same as in the normal biological process of erection, the pump implant should provide an eight-fold increase in the blood flow to the penis to expand the corpora and stretches the surrounding (the tunica). During erection the muscles of the pelvic contract around the base of the corpora cavernosa and the pressure of the blood in the erect penis reaches at least twice the pressure of the blood in the main circulation. At orgasm, the muscle tissue in the corpora cavernosa contracts and the tunica relaxes, the blood drains out of the penis tissue through the dorsal vein leading to a natural deflation of the penis.

In accordance with one preferred embodiment of the present invention, a penile erection pump system is surgically implanted in the lower part of the abdomen and positioned on either side of the penis. The pump inlet connects to an internal artery and the outlet connects to the internal pudendal artery which connects to the dorsal artery feeding blood to the corpus cavernosum of the penis. The pump assembly an inlet that connects to a blood feeding artery, an inlet chamber, a non-return valve assembly, a blood compression chamber and a blood outlet that connects to the artery feeding the penis.

In accordance with another preferred embodiment of the present invention, a penile erection pump implantable near the penis is surgically connected to provide an influx of blood when needed to the internal pudendal artery that feeds the dorsal and deep arteries of the penis.

In accordance with another preferred embodiment of the present invention, an implantable penile erection pump system is surgically placed and connected to the Internal Pudic artery that feeds blood to the corpus cavernosum of the penis. The implanted system maintains the natural blood circulation without restricting blood flow to or from the penis.

In accordance with yet another preferred embodiment of the present invention, an implantable penile erection pump system surgically placed in the lower part of the abdomen on either side of the penis at a position to prevent accidental compression and undesirable forced injection of the blood into the penis.

A principle object of the present invention is to provide a penile erection implant system that is simple, compact, durable and functional without medical supervision after the implant is placed in the body.

Another object of the present invention is to provide an implantable penile erection system that utilizes the biological blood of the body and the erectile organs of the penis to achieve erection state.

Yet it is another object of the present invention is to achieve penile erection state that is physiologically similar to that of the normal male.

It will be understood that anatomy of the penis and artery information disclosed herein is limited to clearly explain the invention. The anatomy of the human body is more and extensively available in the medical text books similar to "Gray's Anatomy".

DESCRIPTION OF A PREFERRED EMBODIMENT

Figure 1:
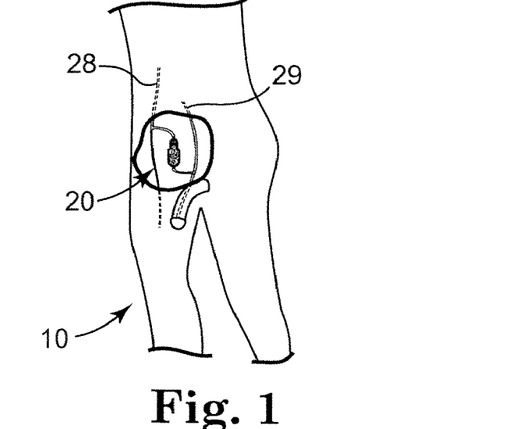
FIG. 1 is a general illustration of surgically implanted pump system for Erectile Dysfunction treatment.
Figure 2A:
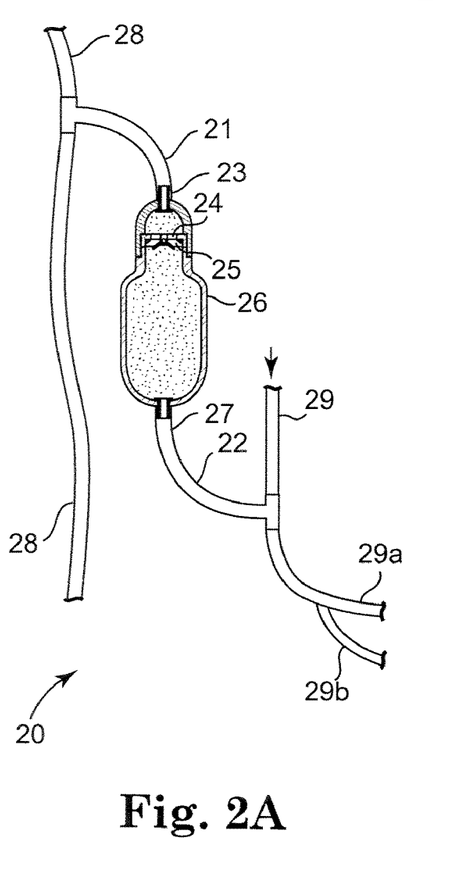
FIG. 2A is an illustration of the preferred pump embodiment shown in its normal blood flow (release) condition.
Figure 2B:
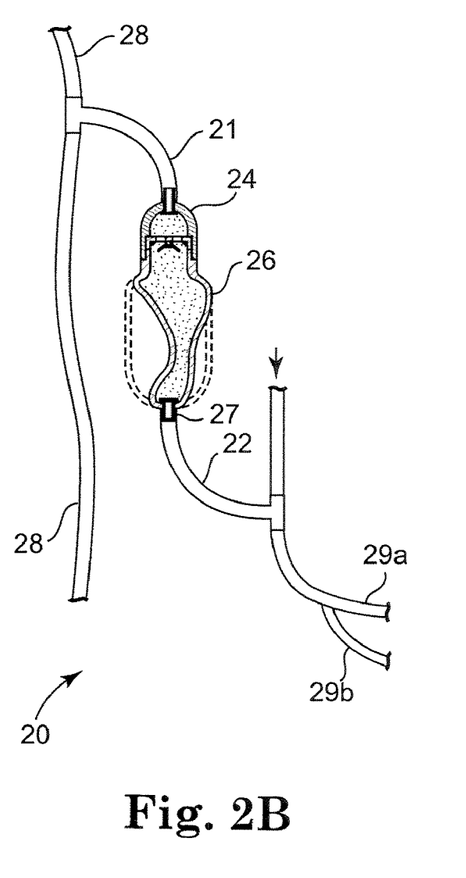
FIG. 2B is an illustration of a preferred pump embodiment shown in its injection (compression) condition.
Figure 3A:
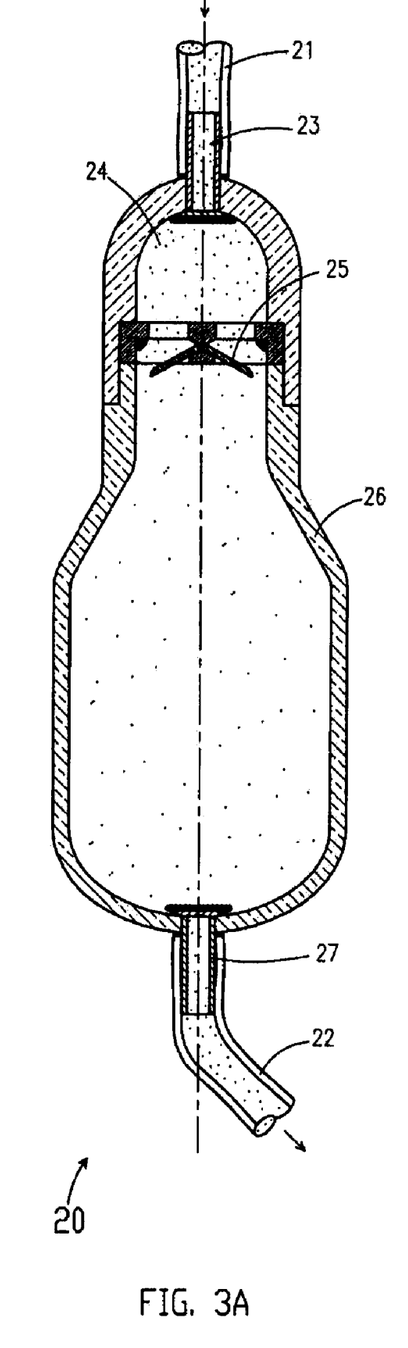
FIG. 3A is an enlarged cross-sectional view of the pump with its compression chamber in normal release condition and the non-return valve in its normal open position.
Figure 3B:
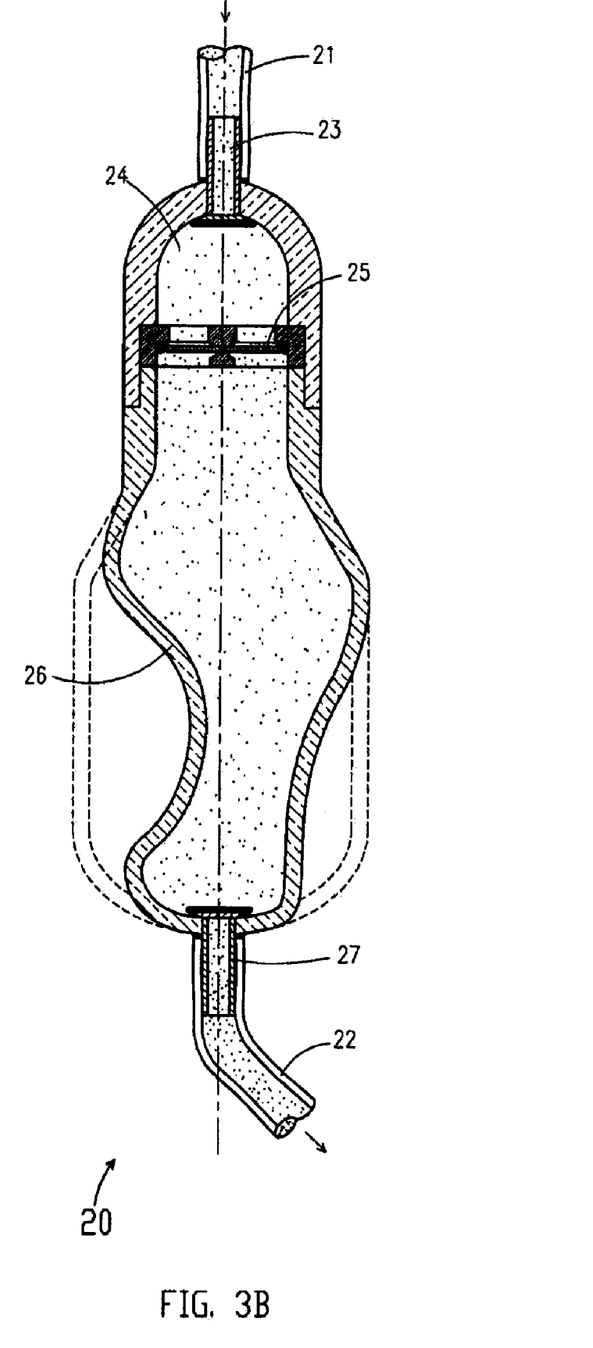
FIG. 3B shows the pump with its compression chamber in the squeeze condition and the non-return valve in closed position.

Referring to the drawings wherein like reference characters are utilized for like parts throughout the several views, a surgically implantable pump system 10 shown in FIG. 1, a preferred embodiment of implantable pump assembly 20, FIG. 2A shows the non-return flapper valve that maintains a unidirectional flow of the blood in its open position during normal blood flow upon release of the compression chamber. FIG. 2B shows the non-return valve in a closed position upon compression of the pump enclosure for injection of the blood into the human penis artery. FIG. 3A and FIG. 3B show views of the preferred embodiment of the pump implant assembly 30.

The pump assembly is advantageously made of biocompatible material that is readily available for implanted devices. The implant is connected to the artery system employing surgically approved stents at two points, one point is in an internal pudendal artery in the lower part of the abdomen, and the second point is in the internal artery at a point before it branches into the dorsal and deep arteries of the penis.

As shown in FIG. 2A and FIG. 2B, the implant 10 includes a preferred embodiment pump implant 20 having inlet artery. connection 21 to be surgically connected to an main artery 28 and an outlet artery connection 22 to be connected to the internal pudendal artery 29 that feeds the dorsal and deep arteries of the penis.

A relatively rigid inlet chamber 24 having an inlet port 23 connected to the inlet artery connection, a non-return valve assembly 25 is fitted between the inlet chamber 24 and an elastic compression chamber 26. The compression chamber 26 is made of a biologically appropriate rubber like material. Each time the user presses the compression chamber 26, the non-return valve 25 closes and the blood contained in the compression chamber 26 is forced out through an outlet port 27 to an artery connection 22 which communicates with the internal pudendal artery that feeds the dorsal and deep arteries of the penis. Each time the patient release the enclosure of the compression chamber 26, its walls springs back to its original position. This creates suction, opens the non return valve and draws blood into the compression chamber 26.

FIG. 2A shows the pump enclosure of the compression chamber 26 in its normal (release) position, and the non-return valve 25 in its normal open position allowing normal flow of the blood. FIG. 2B shows the same pump compression chamber 26 in its squeezed position, and the non-return valve 25 in its closed position preventing back flow of the blood into the inlet chamber 24. Once pressure on the compression chamber is released, the compression chamber wall springs back to its original position as shown by dashed lines.

The pump assembly 20 consists of a relatively rigid inlet chamber 24 having an inlet port 23 connected to the inlet artery connection 21, a non-return valve assembly 25 is fitted between an inlet chamber 24 and an elastic compression chamber 26. The compression chamber 26 is made of a biologically appropriate rubber like material. Each time the patient presses the compression chamber 26, the non-return valve 25 closes and the blood contained in the compression chamber 26 is injected in outlet port 27 to an artery connection 22 which communicates with the internal pudendal artery 29 that branches to the dorsal artery 29a and the deep artery 29b of the penis. Each time the patient release the enclosure of the compression chamber 26, its walls springs back to its original position. This creates suction, opens the non return valve and draws blood into the compression chamber 26.

FIG. 3A shows a cross sectional view of the pump 20 fitted with a preferred embodiment of a fish-tail type non-return flapper valve 25. The pump compression chamber 26 is shown in its normal release state during which the non-return valve 25 remains in its open position allowing blood to flow normally. In FIG. 3B, the elastic compression chamber 26 is shown in a squeezed state during which the non-return valve 25 is in its closed position preventing the blood to flow back into the inlet chamber 24. Upon a sudden increase in pressure in the compression chamber, the valve flaps move toward the valve body in a closed position and seal the valve ports. Upon releasing the enclosure of the compression chamber, it springs back causing pressure differential to move the flaps away from the valve body in an open position. The non return valve assures a unidirectional flow of the pressurized blood out from the compression chamber into the internal artery of the penis.

Figure 4A:
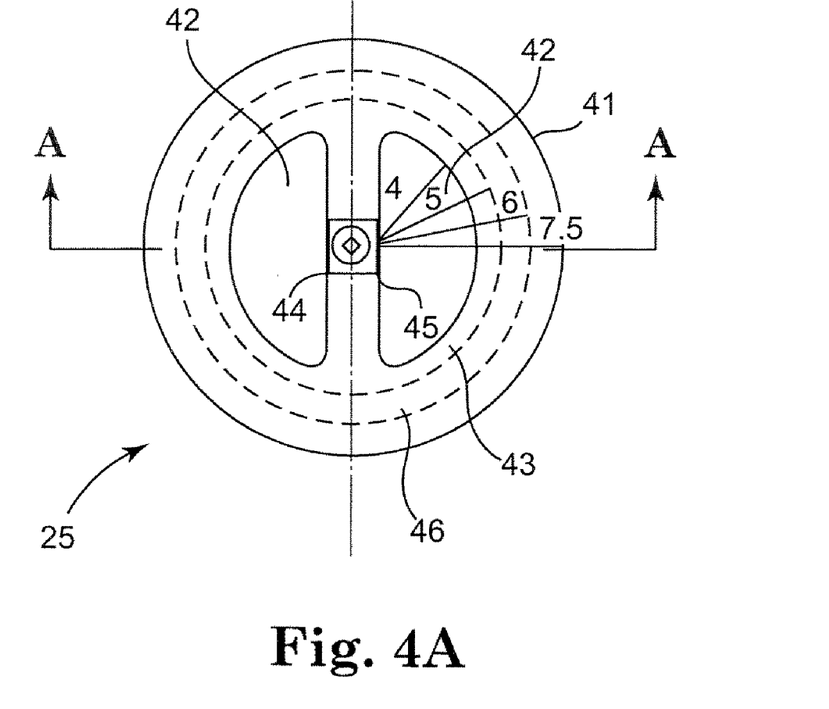
FIG. 4A is an enlarged detail of the sliding disc type non-return flapper valve assembly for use in the pump embodiment of the present invention.
Figure 4B:
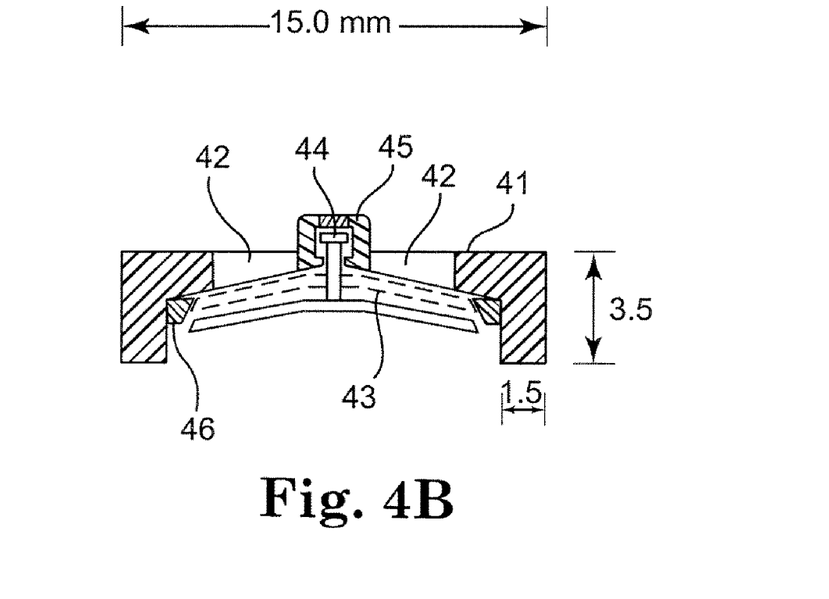
FIG. 4B is a sectional view taken along line A-A of FIG. 4A.

FIGS. 4A and B indicate an enlarged detail of a preferred embodiment of the non-return valve 25 defined as a sliding disc type non-return valve. The valve assembly consists of a valve body 41, having at least one port 42, a sliding disc 43 attached to a shaft stem 44 that slides linearly inside a grooved guide way 45. Under normal blood pressure, the disc 43 stays in an open position apart of the valve body 41. Upon a sudden increase of the blood pressure in the pump elastic compressible chamber (demonstrated by a vertical arrow), the disc moves toward the valve body 41 to a close position indicated by the dashed lines to close the valve ports 42.

Figure 5A:
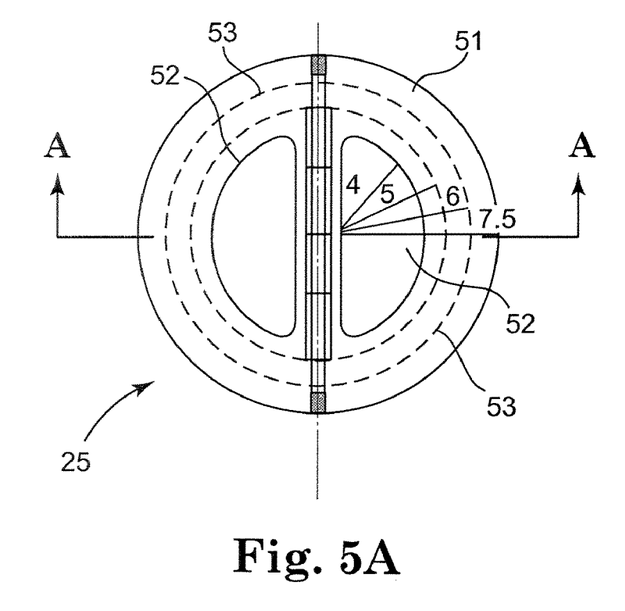
FIG. 5A is an enlarged detail of a tail fish type no-return flapper valve assembly for use in the pump embodiment of the present invention.
Figure 5B:
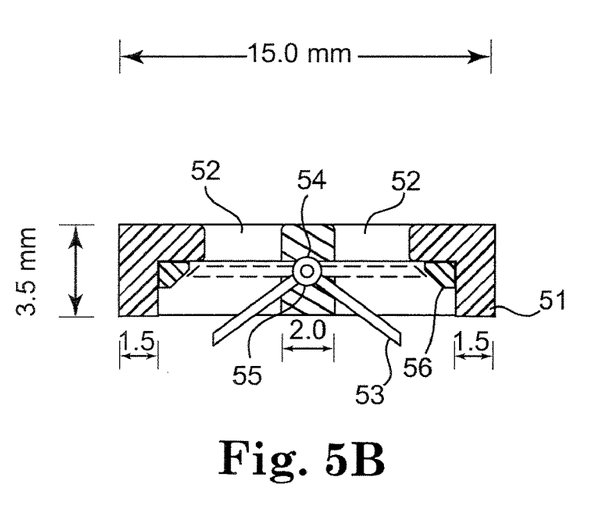
FIG. 5B is a sectional view taken along line A-A of FIG. 5A.
Figure 5C:
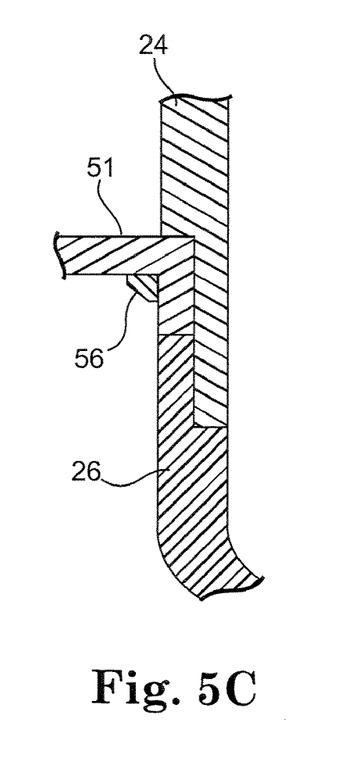
FIG. 5C is view showing the interface of the valve body of FIG. 5A with the inlet and compression chambers of the valve assembly.

FIGS. 5A, 5B, and 5C indicate an enlarged detail of a second preferred embodiment of the non-return valve 25 defined as tail fish type non-return valve. The valve assembly consists of a valve body 51, having at least one port 52, two half circle shaped disc flaps 53 hinged around a center axis mounted pin 54 and having a valve disc stop 55 that limits the open position of the flaps 53. Under normal blood pressure, the flaps 53 stay in an open position apart of the valve body 51. Upon a sudden increase in the blood pressure inside the pump elastic compressible chamber (indicated by a vertical arrow), the flaps swings toward the valve body 51 as indicated by the dashed lines to close the valve ports 52.

Figure 6A:
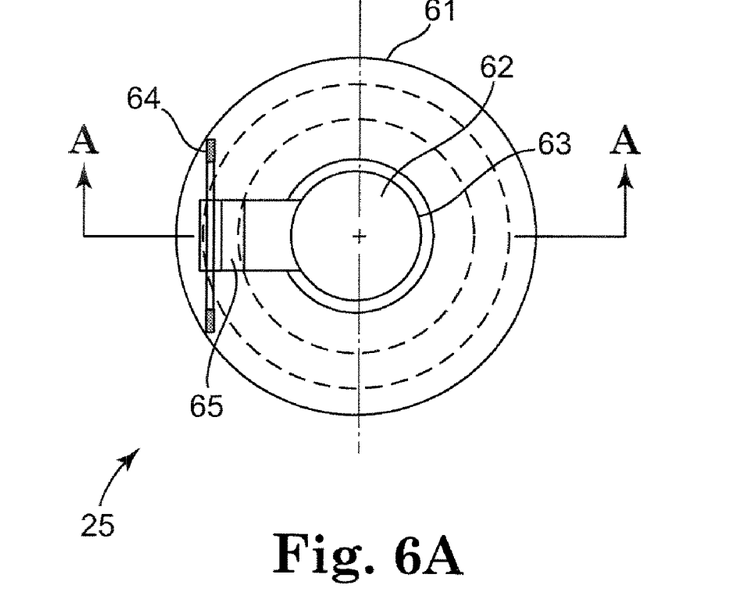
FIG. 6A is an enlarged detail of a swing disc type non-return flapper valve assembly for use in the pump embodiment of the present invention.
Figure 6B:
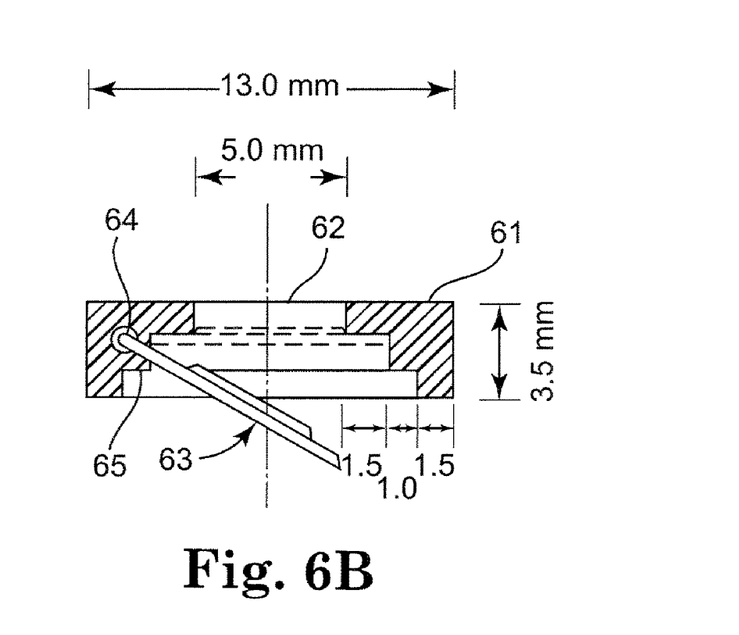
FIG. 6B is a sectional view taken along line A-A of FIG. 6A.

FIGS. 6A and 6B indicate an enlarged detail of a third preferred embodiment of the non-return valve 25 defined as swing disc flap type non-return valve. The valve assembly consists of a valve body 61, having at least one port 62, one circle shaped disc flap 63 hinged on one side around pin 64 and a valve disc stop 65 that limits the open position of the flap 63. Under normal blood pressure, the flaps 63 stay in an open position apart of the valve body 61. Upon a sudden increase in the blood pressure inside the pump elastic compressible chamber (demonstrated by a vertical arrow), the flaps swings toward the valve body 61 as indicated by the dashed lines to close the valve ports 62.

While the present invention has been described with respect to preferred embodiments for implant in the human body to alleviate the erectile dysfunction, those skilled in the art will appreciate a number of variations and modifications there from and it is intended to cover within the appended claims all modifications and variations that fall within the spirit and scope of the present invention. It is also understood that each of the elements described above may singularly or together be useful for other applications in other constructions differing from the types described above.

The above-invention can additionally be described as in the following paragraphs, however, the following paragraphs should be taken as additional exemplary descriptions of the invention and should not be taken as limiting the scope of the invention.

A. A method and procedure for using a pump system implant for treatment of erectile dysfunction comprising:
  a. Surgically implanting and connecting a pump assembly including connections to arteries to communicate blood to the penis.
  b. After a healing period, the patient can achieve erection by manually pressing on a flexible compression chamber of the pump enclosure to effect injecting influx of blood into an outlet port that communicate with the artery to the penis to cause erection.
  c. After orgasm and conclusion of a sexual activity the muscles of the penis normally contract and the blood drains naturally to cause the penis to deflate to a flaccid state.

B. manually pressed or squeezed and springs back to its original shape when released.

C. A slide disc type non-return flapper valve for use with the pump defined in claim number 2, such valve is made of hard biologically safe materials and consists of a valve A human male implantable pump system to be connected to an internal artery from the heart and to an internal artery of the penis providing means to pressurize and inject influx of blood into the penis, the system which comprises:
  a. A pump enclosure having an inlet port that communicates with an inlet chamber and an outlet port that communicates with a compression chamber.
  b. A non return valve fitted in the inlet chamber and communicates with the compression chamber.
  c. An artery connection that communicates with the inlet port and with an internal artery from the heart.
  d. An artery connection that communicates with the outlet port and with an internal artery of the penis.

D. The pump defined in claim 2 wherein the inlet chamber enclosure is made of rigid biologically compatible material that house and protect the non-return valve assembly fitted therein.

E. The pump defined in claim 2 wherein the return valve fitted in the inlet chamber and communicates with the compression chamber maintains a unidirectional flow to prevent the blood contained in the compression chamber to flow backwardly into the inlet chamber.

F. The pump defined in claim 2 wherein the compression chamber enclosure is made of elastic biologically compatible material that flexes inward when body having at least one port and a sliding disc that is free to slide outward to an open position under normal blood pressure and to slide inward to a close position when pressing or squeezing the compression chamber portion of the pump. The valve disc flap moves upon sudden changes in the blood pressure in the compression chamber to maintain unidirectional flow of blood from the inlet chamber into the compression chamber.

G. A fish tail disc type non-return flapper valve for use with the pump defined in claim number 2, such valve is made of hard biologically safe materials and consists of a valve body having at least one port and two half circle shaped disc flaps that are hinged along the center of the valve body and are free to swing outward to an open position under normal blood pressure and to swing inward to a close position when pressing or squeezing the compression chamber portion of the pump. The valve disc flaps move upon sudden changes in the blood pressure in the compression chamber to maintain unidirectional flow of blood from the inlet chamber into the compression chamber.

H. A swing disc type non-return flapper valve for use with the pump defined in claim number 2, such valve is made of hard biologically safe materials and consists of a valve body having at least one port and a circle shaped disc flap that is hinged at one side of the valve body and is free to swing outward to an open position under normal blood pressure and to swing inward to a close position when pressing or squeezing the compression chamber portion of the pump. The valve disc flap moves upon sudden changes in the blood pressure in the compression chamber to maintain unidirectional flow of blood from the inlet chamber into the compression chamber.

What is claimed is:

1. A method for implanting a pump for treatment of erectile dysfunction, the method comprising the steps of:
   providing a manually operable pump having an elastic compression chamber with an inlet port and an outlet port;
   connecting said inlet port to an artery of the human body;
   connecting said outlet port to an artery that is directly or indirectly in blood communication with the corpora cavernosa of the penis; and
   placing said pump in an interior cavity of the body.

2. The method of claim 1, wherein said inlet port of said pump communicates with an inlet chamber to the compression chamber and said outlet port of said pump communicates with the compression chamber.

3. The method of claim 2, wherein said pump further includes a non-return valve that is fitted within the inlet chamber and is in communication with said compression chamber.

4. The method of claim 3, wherein said non-return valve maintains a unidirectional flow to prevent blood contained in the compression chamber from flowing backwardly into said inlet chamber.

5. The method of claim 2, wherein said compression chamber is configured to be squeezable from an original inflated shape and to spring back to its original inflated shape when the squeeze on the compression chamber is released.

6. The method of claim 1, wherein said pump further includes a non-return valve.

7. An implantable means for obtaining a penile erection, said means comprising:
   first connecting means for connecting with and receiving blood from an artery of the human body;
   second connecting means for interfacing with said first connecting means and for directly or indirectly connecting with an artery that delivers blood to the corpora cavernosa of the penis;
   compressing means for transferring blood obtained in said first connecting means to said second connecting means and for transferring blood from said second connecting means to the corpora cavernosa to cause an erection.

8. The implantable means of claim 7, wherein said compressing means additionally being compressible from an original inflated state and returning back to the original inflated shape when compression is released.

9. The implantable means of claim 7, wherein said compressing means includes means for preventing backflow of blood from said second connecting means to said first connecting means.

10. A human male implantable pump system to be connected between an internal artery from the heart and an internal artery of the penis providing means to pressurize and inject influx of blood into the penis, the system which comprises:

a manually operable pump enclosure having an inlet port that communicates with an inlet chamber and an outlet port that communicates with an elastic compression chamber;

a non return valve fitted in the inlet chamber and communicates with the compression chamber;

an artery connection that communicates with the inlet port and adapted to communicate with the internal artery from the heart; and an artery connection that communicates with the outlet port and adapted to communicate with the internal artery of the penis.

11. The system of claim 10, wherein said non-return valve maintains a unidirectional flow to prevent blood contained in the compression chamber from flowing backwardly into said inlet chamber.

12. The system of claim 10, wherein said compression chamber is configured to be squeezable from an original inflated shape and to spring back to its original inflated shape when the squeeze is released.

* * * * *